(12) United States Patent
Pallazza

(10) Patent No.: US 7,479,149 B2
(45) Date of Patent: Jan. 20, 2009

(54) BALLOON CONFIGURING APPARATUS

(75) Inventor: Stefan M. Pallazza, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 305 days.

(21) Appl. No.: 09/682,865

(22) Filed: Oct. 25, 2001

(65) Prior Publication Data

US 2003/0083687 A1    May 1, 2003

(51) Int. Cl.
*A61M 29/00* (2006.01)
(52) U.S. Cl. .................. 606/191; 604/96.01; 604/509
(58) Field of Classification Search ........... 606/108, 606/191, 192, 194, 195, 198, 201, 158, 159
See application file for complete search history.

(56) References Cited

U.S. PATENT DOCUMENTS

| 4,183,102 | A | * | 1/1980 | Guiset ...................... 623/1.25 |
| 4,990,139 | A | * | 2/1991 | Jang ....................... 604/101.01 |
| 5,087,246 | A | | 2/1992 | Smith ........................... 604/96 |
| 5,226,887 | A | | 7/1993 | Farr et al. ...................... 604/96 |
| 5,318,587 | A | | 6/1994 | Davey ......................... 606/194 |
| 5,320,634 | A | | 6/1994 | Vigil et al. ................... 606/159 |
| 5,350,361 | A | * | 9/1994 | Tsukashima et al. ... 604/103.07 |
| 5,415,635 | A | * | 5/1995 | Bagaoisan et al. ..... 604/101.05 |
| 5,783,227 | A | | 7/1998 | Dunham ..................... 425/318 |
| 5,899,917 | A | * | 5/1999 | Edwards et al. ............. 606/195 |
| 6,013,092 | A | | 1/2000 | Dehdashtian et al. ........ 606/194 |
| 6,033,380 | A | | 3/2000 | Butaric et al. ................... 304/96 |
| 6,077,273 | A | * | 6/2000 | Euteneuer et al. ........... 606/108 |
| 6,123,712 | A | * | 9/2000 | Di Caprio et al. ........... 606/108 |
| 6,126,652 | A | | 10/2000 | McLeod et al. ................ 606/1 |
| 6,136,011 | A | * | 10/2000 | Stambaugh .................. 606/159 |
| 6,296,655 | B1 | * | 10/2001 | Gaudoin et al. ............. 606/194 |

FOREIGN PATENT DOCUMENTS

WO        01/21103        3/2001

* cited by examiner

*Primary Examiner*—Julian W Woo
*Assistant Examiner*—Victor X Nguyen
(74) *Attorney, Agent, or Firm*—Vidas, Arrett & Steinkraus

(57) ABSTRACT

A device for configuring an inflatable balloon of a balloon catheter assembly comprises a body with a plurality of inflatable members defining a channel therebetween. The channel is sized to accommodate at least a portion of a balloon catheter therein. Each inflatable member has a balloon contacting portion.

29 Claims, 10 Drawing Sheets

BALLOON CONFIGURING APPARATUS

BACKGROUND OF INVENTION

Medical balloons are used in the body in a variety of applications including as dilatation devices for compressing plaque and for expanding prosthetic devices such as stents at a desired location in a bodily vessel. Because it is typically necessary for the balloon to traverse a tortuous anatomy as it is being delivered to the desired location in the bodily vessel, it is desirable for the balloon to assume as low a profile as possible.

One way to achieve a low profile is by folding the balloon to form a number of wings. In accordance with the prior art, wings may be formed in a partially inflated balloon by imparting an inward radial force about the periphery of the balloon using a plurality of rigid blades which are distributed about the periphery of the balloon. As the blades move radially inward, wings are formed in the balloon.

When forming wings in balloons in this manner, however, special care must be taken to ensure that the blades do not have any sharp edges or burrs which would damage the balloon. Also, caution must be exercised to prevent the blades from applying damaging forces to the balloon and/or any structures underlying the balloon such as markerbands, bonds or hubs. Although the amount of force applied to the balloon may be reduced to avoid damaging the balloon and/or any underlying structures, sufficient force must, nevertheless, be applied to completely form the balloon wings so as to achieve the desired cross-section. As such, a great deal of precision is needed in determining the closed position of the blades. The problem is exacerbated when a single device is to be used to fold balloons on catheters of different cross-sections.

There remains a need for innovative devices for forming balloon folds and for innovative devices which may be used to form balloon folds on catheters of different cross-sections.

All US patents and applications and all other published documents mentioned anywhere in this application are incorporated herein by reference in their entirety.

Without limiting the scope of the invention in any way, the invention is briefly summarized in some of its aspects below. Additional details of the invention and/or additional embodiments of the invention may be found in the Detailed Description of the Invention below.

A brief abstract of certain aspects of the technical disclosure in the specification is provided as well for the purposes of complying with 37 C.F.R. 1.72.

SUMMARY OF INVENTION

In one embodiment, the invention is directed to a device for configuring an inflatable balloon of a balloon catheter assembly. The device comprises a body which comprises a plurality of inflatable members defining a channel therebetween. The channel is sized to accommodate at least a portion of a balloon catheter. Each inflatable member has a balloon contacting portion. Upon inflation of the inflatable members, the balloon contacting portions apply an inward force to a balloon catheter disposed in the channel. Desirably, the inflatable members are disposed about the circumference of a circle. Typically, the device comprises three to twelve inflatable members. The inflatable members may take on any configuration to provide an appropriate balloon contacting portion. Some non-limiting examples of suitable configurations include generally tubular inflatable members having circular cross-sections and generally tubular inflatable members having wedge-shaped cross-sections.

The inflatable members may be disposed in numerous configurations about the channel. In one configuration, the plurality of inflatable members may include at least two inflatable members which are disposed end-to-end along the length of the channel. In another configuration, the inflatable members may be disposed in one or more spirals about the channel where it is desired to provide spiral folds in a balloon. In yet another configuration, the inflatable members may include at least two inflatable members which are circumferentially and axially displaced from one another. Desirably, inflatable members which are circumferentially and axially displaced from one another are shorter in length than the balloon.

The device may further comprise a housing comprising one or more housing members in which the inflatable members are disposed. The housing constrains the inflatable members and allows the inflatable members to apply the necessary force to the balloon. Typically, the housing will be in the form of a rigid tube with optional first and second end caps. Desirably, the first end cap is disposed at the first end of the rigid tube across a first opening of the rigid tube and the second end cap disposed at the second end of the tube across a second opening and the inflatable members contact the first and second end caps. In some embodiments, the first and second end caps can support the inflatable members and serve to align the inflatable members. Typically, at least one of the end caps will have an opening therethrough sized to receive at least a portion of a balloon catheter therethrough.

The invention is also directed to a device for configuring an inflatable balloon of a balloon catheter assembly, where the device includes a body comprising an inflatable member having a balloon contacting portion and a catheter support member constructed and arranged relative to the body to support a catheter in a region adjacent the balloon contacting portion of the inflatable member.

The inflatable member optionally comprises a plurality of balloon contacting portions. The balloon contacting portions are desirably spaced about the circumference of a circle and the catheter support member is constructed and arranged to support a catheter in a region between the balloon contacting portions.

The device may further comprise one or more constraining members which constrain the inflatable member and allow the inflatable member to apply the necessary force to the balloon. Optionally, the constraining members may be in the form of a plurality of slats each of which is disposed between adjacent balloon contacting portions.

Typically, a housing will be provided. A suitable housing in the form of a rigid tube having a first end with a first opening and a second end with a second opening and a passage therethrough may be used.

In another embodiment, the device may comprise a plurality of inflatable members each of which has a balloon contacting portion. The inflatable members are disposed about the circumference of a circle and the catheter support member is constructed and arranged to support a catheter in a region between the balloon contacting portions.

The invention is also directed to method of configuring a medical balloon. In accordance with the invention, a medical balloon may be disposed between the inflatable members of any of the inventive devices disclosed herein and the medical balloon at least partially inflated. The inflatable members are then inflated so that the balloon contacting portions deform portions of the medical balloon inward. The medical balloon is at least partially deflated and desirably, completely deflated with the inwardly deformed portions of the medical balloon forming a plurality of balloon folds. Finally, the inflatable members are removed from about the medical balloon.

In another embodiment of the inventive method, a catheter comprising a medical balloon is provided and a plurality of inflatable members are disposed about the medical balloon. Each inflatable member has a balloon contacting portion. The balloon is at least partially inflated by supplying an inflation fluid thereto and the inflatable members are at least partially inflated so that the balloon contacting portions contact the medical balloon and apply an inward force to the medical balloon. At least some of the inflation fluid may be removed from the medical balloon and the inflatable members may be removed from about the medical balloon. Desirably, the inflatable members are configured to apply a radially inward force to the medical balloon when they are inflated. More desirably, the inflatable members are symmetrically disposed about the medical balloon and upon inflation apply a sufficient radially inward force to the medical balloon to form a plurality of indentations in the medical balloon. The medical balloon upon removal of the inflation fluid therefrom has a plurality of folds.

In yet another embodiment of the inventive method, a catheter comprising a medical balloon may be provided. An inflatable member with a plurality of balloon contacting portions is disposed about the medical balloon. The inflatable member is at least partially inflated so that the balloon contacting portions of the inflatable member contact the medical balloon and apply an inward force to the medical balloon. The medical balloon may be at least partially deflated and desirably completely deflated and the medical balloon removed from between the balloon contacting portions.

In accordance with the inventive methods, the inward force may be applied to the balloon in a variety of ways. For example, the inward force may be applied progressively along the length of the balloon. This may be accomplished by providing inflatable members which have inflation lumens which open into the inflatable members at a first end of the device and a balloon which has an inflation lumen which opens into the balloon at the second end of the device, opposite the first end of the device.

Further in accordance with the inventive methods, the inflatable members may be inflated simultaneously or in a predetermined sequence. As an example of the latter, where the plurality of inflatable members includes a first inflatable member located at a first end of the balloon, a second inflatable member located at the middle of the balloon and a third inflatable member located at a third end of the balloon, the second inflatable member may be inflated prior to the first and third inflatable members to configure the middle of the balloon prior to configuring the ends of the balloon. As another example of the latter, the inflatable member may be inflated prior to the second inflatable member which may be inflated prior to the third inflatable member to progressively configure the balloon from one end to the other end.

The invention is also directed to a method of configuring at least a portion of a medical balloon comprising the steps of providing a catheter comprising a medical balloon, at least partially inflating the medical balloon, applying a plurality of discrete axially spaced inward forces to the medical balloon and deflating the medical balloon. Suitably, the plurality of discrete forces are applied by a plurality of inflatable members axially spaced along the balloon. The plurality of discrete forces may be applied simultaneously with one another or in a predetermined sequence.

The inventive methods may be used to provide folds along the entire length of the balloon or along a portion of the length of the balloon. The inventive methods may be used to provide folds with complex shapes such as spirals as well as other complex shapes.

The invention is also directed to a medical balloon comprising a pleat, at least a portion of which extends in a direction which is non-parallel to the longitudinal axis of the balloon. Desirably, the pleat has a first end and a second end, the first end circumferentially and longitudinally displaced from the second end of the pleat. In one embodiment, the pleat spirals at least partially about a longitudinal axis of the balloon. The balloon may optionally comprise a plurality of pleats each of which has a first end and a second end which is circumferentially and longitudinally displaced from the first end. The pleats may be longitudinally discontinuous or continuous.

The invention is also directed to a medical balloon having a body portion with a first region with pleating and a second region with pleating where the second region is axially displaced from the first region and the pleating in the second region differs in appearance from the pleating in the first region. The pleating in the second region may differ in appearance from that of the first region as a result of discontinuities between the pleating in the first and second regions. The appearance of the pleating in the first and second regions may also differ in that the number of pleats in the first region differs from the number of pleats in the second region. It is also within the scope of the invention for the shape of the pleating in the different regions to differ. The medical balloon may optionally comprise additional pleated regions where the appearance of the pleating differs from the appearance of the pleating in other regions.

The invention is further directed to medical balloons manufactured using any of the inventive techniques disclosed herein.

Additional details and/or embodiments of the invention are discussed below.

DETAILED DESCRIPTION

Figure 1:
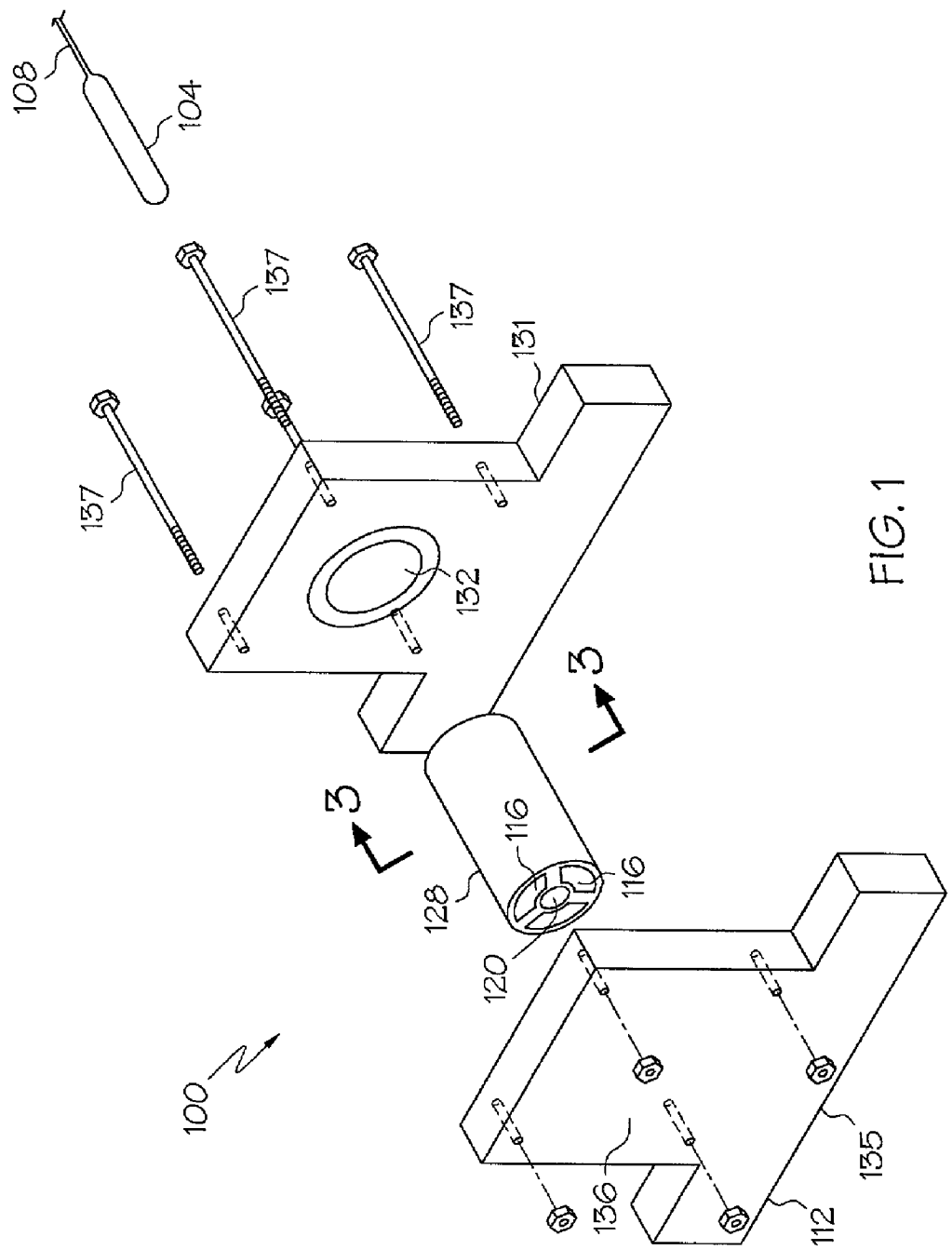
FIG. 1 is an exploded view of an inventive device for configuring an inflatable balloon in accordance with an embodiment of the invention.
Figure 2:
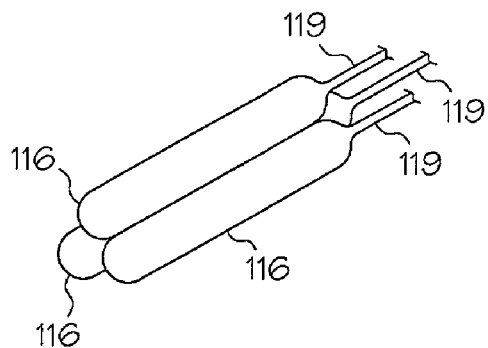
FIG. 2 shows a plurality of inflatable members for use in the inventive device of FIG. 1.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, unless otherwise indicated, identical reference numerals used in different figures refer to the same component.

Figure 3:
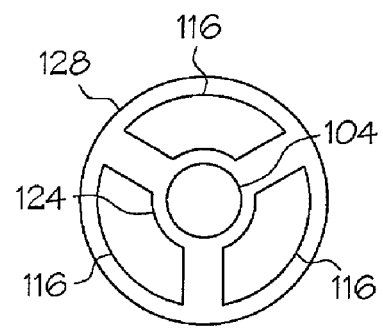
FIG. 3 shows a cross-sectional view of the inventive device of FIG. 1 taken along line 3-3.

In one embodiment, the invention is directed to a device such as that shown generally at 100 in FIGS. 1-3, 6 and 7 for configuring an inflatable balloon 104 of a balloon catheter assembly 108. Balloon catheter assembly 108 comprises catheter tube 109 and balloon 104 disposed thereabout. Device 100 comprises a body 112 with a plurality of inflatable members 116 defining a channel 120 therebetween. In this embodiment, inflatable members 116 are disposed about the circumference of a circle, as shown in FIG. 3. Channel 120 is sized to accommodate at least a portion and desirably, the entirety of balloon 104 of balloon catheter 108 therein. Each inflatable member 116 has a balloon contacting portion 124. Device 100 typically comprises from three to six inflatable members 116. Additional inflatable members 116 may be provided. The invention contemplates providing at least one inflatable member.

Figure 4:
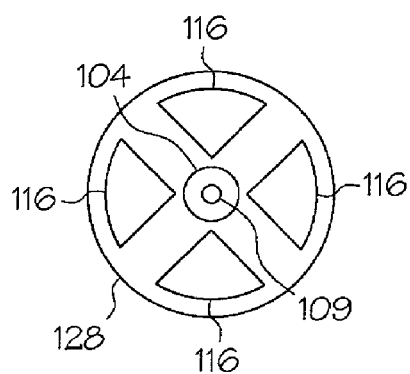
FIG. 4 shows a cross-sectional view similar to that of FIG. 3 of an inventive device having pie-shaped inflatable members.
Figure 5:
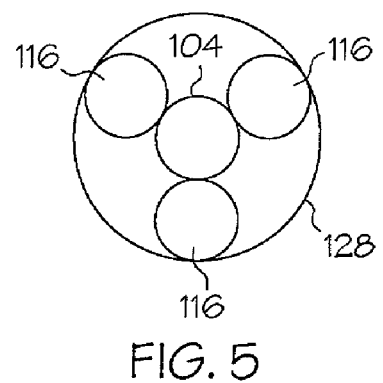
FIG. 5 shows a cross-sectional view similar to that of FIG. 3 of an inventive device having circular inflatable members.

Inflatable members 116 may take on any configuration to provide an appropriate balloon contacting portion. Some non-limiting examples of suitable configurations include a generally tubular inflatable member having a wedge-shaped cross-section as shown in FIG. 3, a generally pie-shaped section as shown in FIG. 4, a circular cross-section as shown in FIG. 5 and a V-shaped cross-section (not shown). Typically, the balloon contacting portion will be rounded, radiused, pointed, flat or of other suitable shape regardless of the shape of the non-contact surface.

Inflatable members 116 may be in the form of a thick walled silicone tube capable of withstanding multiple inflation and deflation cycles. Inflatable member 116 may also be made of any other suitable balloon materials including compliant and non-compliant materials such as latex, polyethylene terephthalate (PET), polyethylene, nylon and polyvinyl chloride. The inflatable member may be made of the same material as the balloon which is to be configured or may be made of a different material. In the former case, the inflatable member must be inflated to a pressure exceeding that of the balloon as the balloon is configured. Optionally, the inflatable member will be made of a material which is harder and/or more rigid than the balloon to be folded. Materials which are softer and/or less rigid than the balloon may also be used.

Figure 8:
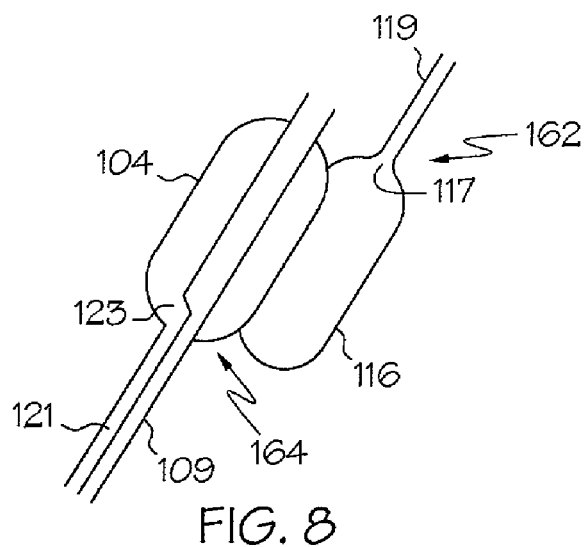
FIG. 8 shows a cross-sectional view of a balloon and an inflatable member.

Inflatable members 116 are supplied with a compressible or non-compressible inflation fluid via inflation lumens 119. As shown in FIG. 8, inflation lumen 119 typically opens into inflatable member 116 via an inflation port 117 which is located at a first end of the inventive device. Balloon 104 is supplied with a compressible or non-compressible inflation fluid via inflation lumen 120 which opens into balloon 104 via inflation port 123 at a second end of the device generally opposite the first end of the device. With this arrangement of inflation ports, inflatable members 116 may configure balloon 104 progressively along the length of the balloon from the first end of the balloon to the second end of the balloon, with inflation fluid gradually forced out inflation port 123. The arrangement of having inflation port 123 of inflatable member 116 and balloon 104 at opposing ends allows for optimal removal of balloon inflation fluid. The gradual bleeding of inflation fluid from a single end of the balloon reduces the likelihood of formation of bulges or bubbles in the balloon.

Figure 9:
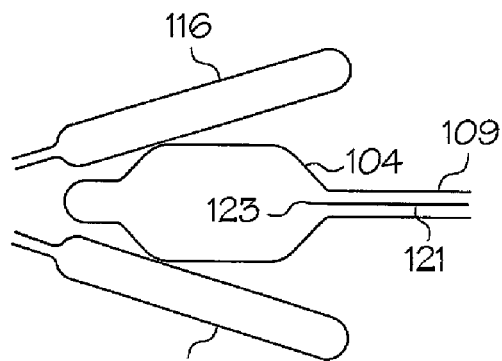
FIG. 9 shows an inventive device with inflatable members disposed at an angle relative to the balloon.

The inventive devices may also be provided in embodiments, such as that shown generally at 100 in FIG. 9, in which inflatable members 116 are held at an oblique angle relative to the longitudinal axis of balloon 104. As inflatable members 116 are inflated, balloon is gradually configured along its length and the inflation fluid in balloon 104 forced to exit from inflation port 123 opposite to where configuring of the balloon commences.

Figure 9A:
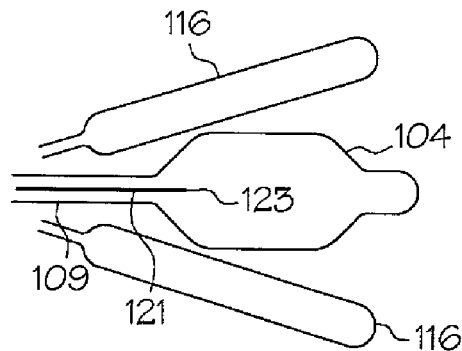

Alternatively, as shown in FIG. 9a, inflatable members 116 may also be angled so that as it is expanded, the closed end of balloon 104 is compressed first and the lumen end of balloon 104 is compressed last.

Other arrangements of the inflation ports are also within the scope of the invention. By way of example only, all of the inflation ports may be located in the middle of the balloon and inflatable members.

The inflation fluid may be in the form of a gas or a liquid and may be at room temperature, cooled or heated. Optionally, a controller may be provided to control the temperature of the inflation fluid. Where the inflatable member is made of a material characterized by a glass temperature $T_g$ or a crystallization temperature $T_c$, the inflation fluid may suitably be heated, but the temperature should remain below that of the $T_g$ or $T_c$ of the inflatable member to prevent deformation. Typically, in cases where the inflation fluid for the inflatable members is heated, the fluid will be heated to a temperature in excess of the temperature of the balloon which is being configured so that the inflatable members are warmer than the balloon. When the warmed inflatable members contact the balloon, the balloon is warmed and preferentially softened in the region of the inflatable members as compared with the remainder of the balloon thus facilitating configuring of the desired region of the balloon. The balloon may also be at least partially inflated with an inflation fluid which is cooler than the inflation fluid delivered to the inflatable members in order to preserve any internal structure in the balloon.

A controller may also be used to control the pressure of the inflation fluid, the rate of increase and/or decrease of the pressure of the inflation fluid as well as the period of time in which the pressure is maintained. The period of time in which the pressure is maintained will depend on a variety of factors including the pressure of the inflation fluid and the relative temperatures of the inflatable members and the balloon.

Device 100 may further comprise a housing 128 in which inflatable members 116 are constrained. Typically, the housing will be in the form of a rigid tube which may be made of any suitable material which is capable of constraining the inflatable member including metal, glass, rubber or plastic. Desirably, housing 128 will be made of a clear material to allow for monitoring of the balloon as it is configured.

Figure 6:
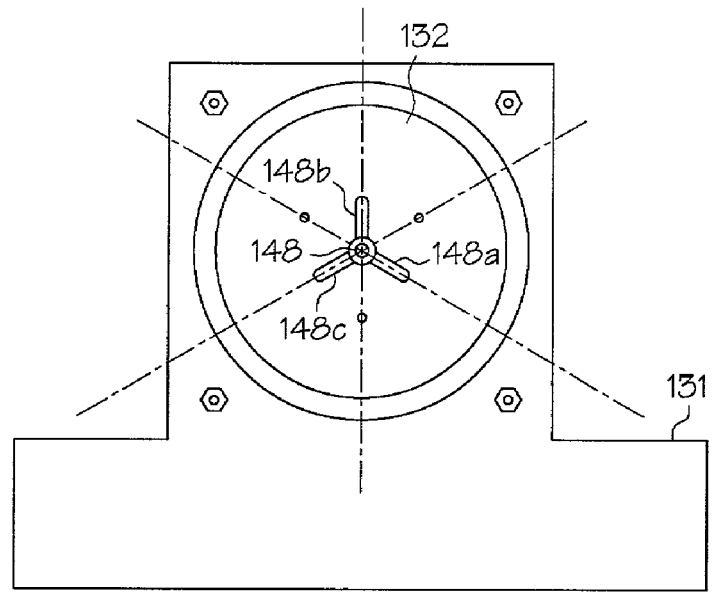
FIG. 6 shows a first end view of the inventive device of FIG. 1.
Figure 7:
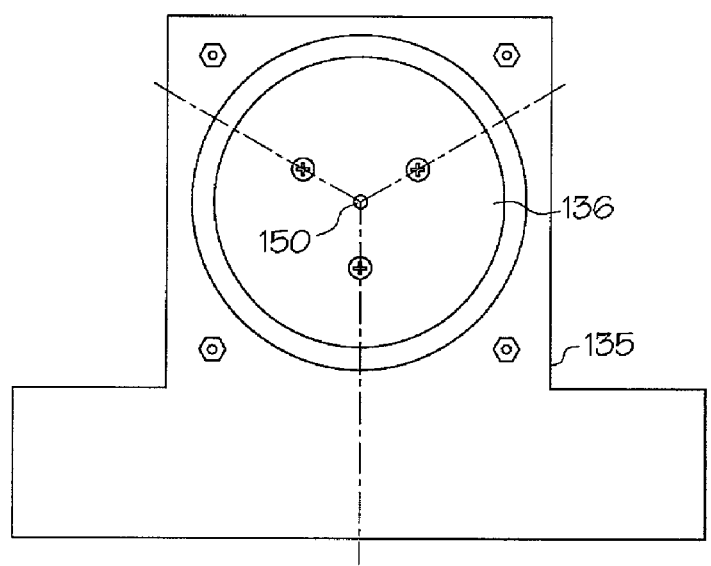
FIG. 7 shows a second end view of the inventive device of FIG. 1.

In one embodiment of the invention, as shown in FIGS. 1, 6 and 7, device 100 may further comprise first end support 131 including first end cap 132 and second end support 135 including second end cap 136. In the illustrated embodiment, first end cap 132 is disposed at a first end of housing 128, second end cap 136 is disposed at a second end of housing 128 and inflatable members 116 extend between the first and second end caps. Optionally, the first and second end caps may support the inflatable members and serve to align the inflatable members. As shown in FIG. 1, one or more optional connecting members 137, in the form of bolts, join the first and second end supports. Other types of connecting members may also be used if desired. For example, the body portion of the device including the first and second end supports may be of one piece construction (not shown) or may be joined by a base member (not shown). The device may also be provided without any additional connectors between the first and second end supports. The end supports may also be adhesively joined or otherwise joined to the rigid tube or may be integrally formed with the rigid tube.

At least one of the end caps, desirably, first end cap 132, has an opening 148 therethrough sized to receive the balloon portion of the balloon catheter therethrough. As shown in FIG. 6, opening 148 is configured to allow removal of a winged balloon therethrough. Opening 148 is shown having three portions 148a-c corresponding to the winged portion of a balloon. Opening 148 may be provided with additional portions to accommodate in excess of three balloon folds or with fewer portions. Opening 148 can assume any other shape which would allow for removal of a balloon from the apparatus.

Desirably, second end cap 136 also includes a recess or an opening 150 therethrough for supporting a portion of the balloon catheter in a region adjacent balloon contacting portion 124 of inflatable member 116. In embodiments without a second end cap, an optional opening for supporting a portion of the balloon catheter may be provided directly in the second end support.

In the embodiment of FIGS. 1-3, 6 and 7, three inflatable members 116 are provided, each with a balloon contacting portion. Typically, at least three to twelve or more balloon contacting portions will be provided. As few as a single balloon contacting portion may be provided where it is desired to place a single pleat in a balloon.

Balloon contacting portions are desirably spaced about the circumference of a circle. More desirably, the balloon contacting portions are spaced regularly about the circumference of the circle.

It is further within the scope of the invention to provide a device comprising a plurality of segments each of which comprises inflatable members. Such a device is capable of providing more complicated pleats in a balloon. An example of such a device comprising two segment of inflatable members 116a and 116b is shown in longitudinal cross-section at 100 in FIG. 10. Each half of balloon 104 may be configured independently of the other half. In one embodiment, the device of FIG. 10 may be used to gradually configure a balloon by initially configuring half of the balloon using inflatable members 116a and subsequently configuring the other half of the balloon using inflatable members 116b. Using this embodiment, the first and second segments of the device may differently configure each end of the balloon.

Figure 11A:
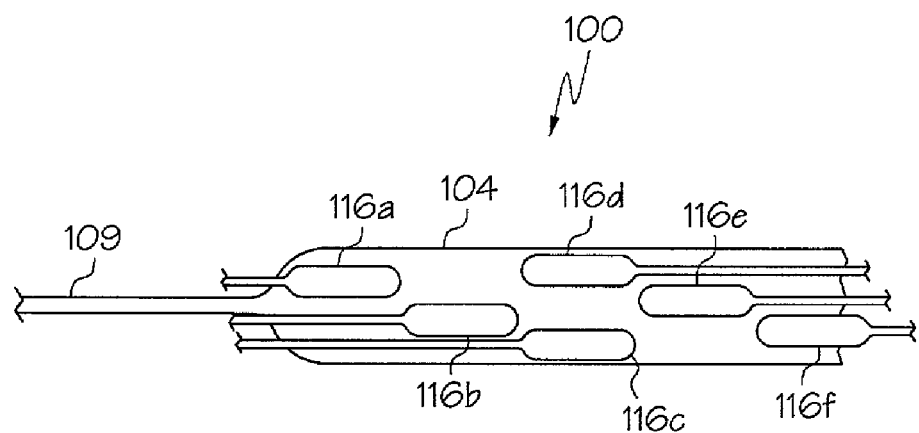
FIG. 11*a* shows an inventive device with inflatable members disposed spirally about a balloon.
Figure 11B:
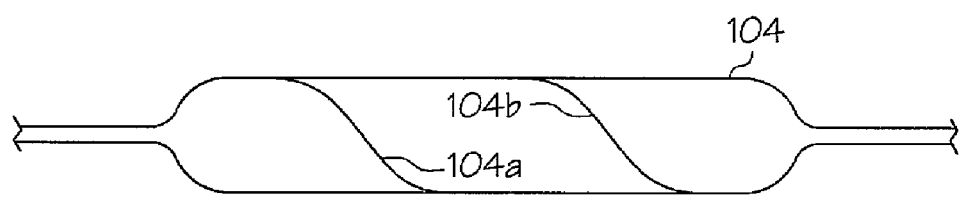
FIG. 11*b* shows a perspective of a balloon configured with the device of FIG. 11*a*.

In yet another embodiment of the invention, shown generally at 100 in FIG. 11a, a plurality of inflatable members including members 116a-f are disposed spirally along the length of balloon 104. Upon inflation of inflatable members 116, a plurality of spiral pleats 104a and 104b are placed in balloon 104, as shown in FIG. 11b.

Other arrangements of inflatable members which are capable of providing more complex shaped pleats are within the scope of the invention as well. Circumferential pleats, for example, may be formed by providing a device with a plurality of donut shaped inflatable members about the balloon and inflating the inflatable members.

Figure 12:
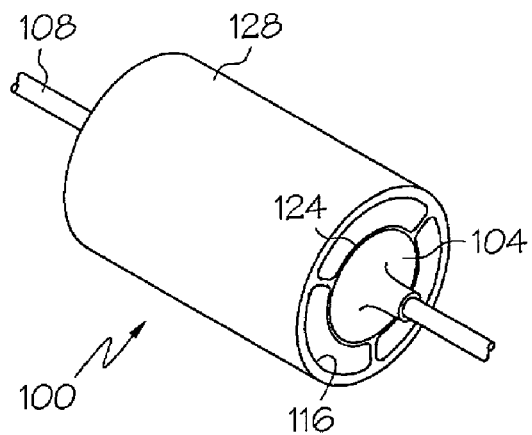
FIG. 12 shows a perspective of an inventive device with a balloon disposed therein.
Figure 13:
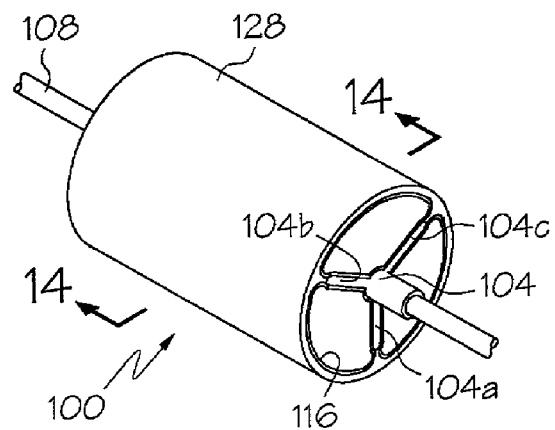
FIG. 13 shows a perspective view of the inventive device of FIG. 12 with the inflatable members inflated to produce a plurality of wings in the balloon.
Figure 14:
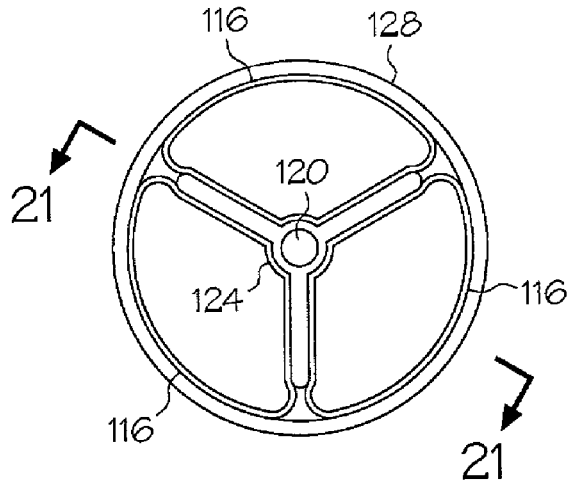
FIG. 14 shows a cross-sectional view of the inventive device of FIG. 13 taken along line 14-14.
Figure 15:
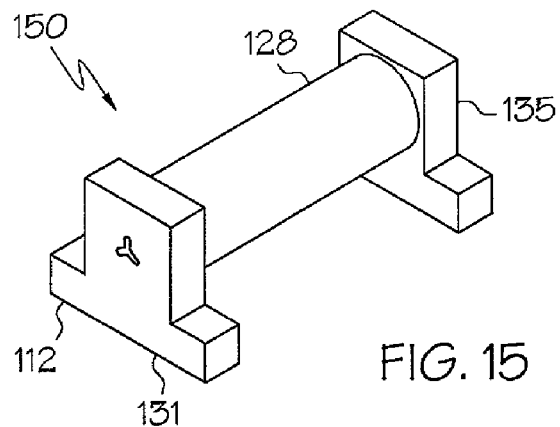
FIG. 15 shows a perspective of an inventive device for configuring an inflatable balloon in accordance with another embodiment of the invention.
Figure 16:
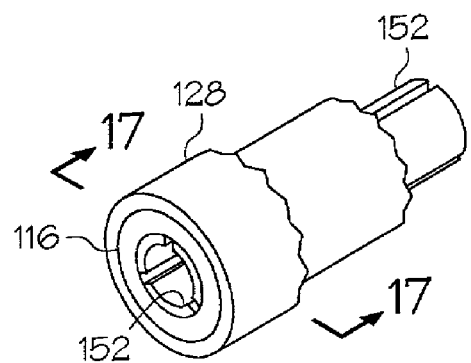
FIG. 16 shows a perspective view of the rigid tube and inflatable member of FIG. 15 with parts cut-away.
Figure 17:
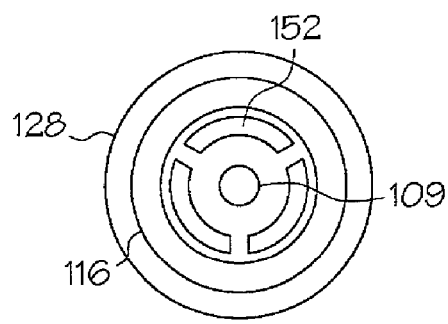
FIG. 17 shows a cross-sectional view of the rigid tube and inflatable member of FIG. 16 taken along line 17-17.
Figure 18:
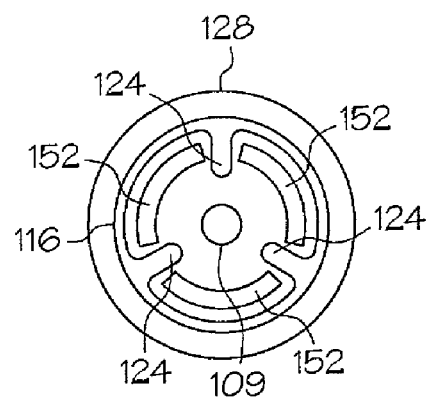
FIG. 18 shows the cross-sectional view of FIG. 17 with the inflatable member at least partially inflated.

In use, as shown in FIG. 12, balloon portion 104 of catheter 108 is inserted in channel 120 between inflatable members 116. Balloon portion 104 is at least partially inflated. In the view of FIG. 12, optional first and second end supports are not present. An inflation fluid is supplied to inflatable members 116 to expand inflatable members 116 inward, as shown in FIG. 13 and in transverse cross-section in FIG. 14. As inflatable members 116 expand inward, they apply an inward force to those portions of balloon 104 that they contact. When inflation of inflatable members 116 is complete, balloon 104 includes a plurality of winged portions 104a-c. Balloon 104 may then be removed from device 100.

Figure 19:
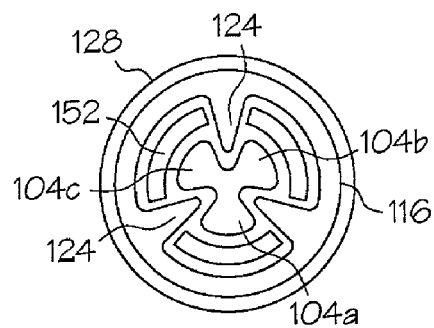
FIG. 19 shows a cross-sectional view of FIG. 18 with the inflatable member inflated and forming a plurality of wings in a balloon.

The invention is also directed to a device such as that shown generally at 100 in FIGS. 15-19 for configuring an inflatable balloon of a balloon catheter assembly. Device 100 comprises a body 112 with first end support 131 and second end support 135 and a housing 128 extending therebetween. Typically, housing 128 is in the form of a rigid tube. One or more inflatable members 116 having a balloon contacting portion 124 are disposed in housing 128. In the embodiment of FIGS. 15-18, a single inflatable member 116 is provided. Adjacent balloon contacting portions are separated by constraining members 152, desirably in the form of slats between balloon contacting portions 124. On expansion of inflatable member 116, only balloon contacting portions 124 are free to expand inward between adjacent constraining members to contact the balloon, the remainder of the balloon prevented from expanding inward by the constraining members. As shown in FIG. 19, inflatable member 116 has been inflated and balloon contacting portions 124 have formed wings 104a-c in balloon 104.

The invention also contemplates embodiments in which inflatable member 116 is constructed with weaker and stronger portions such that upon inflation, only selected portions of the inflatable member, for example, the balloon contacting portions, expand inward, thereby obviating the need for constraining members. The inflatable member may also be provided with a thinner or weaker wall in the vicinity of the balloon contacting portions. Embodiments having an inflatable member with a rigid outer portion may be provided without a housing.

Figure 20:
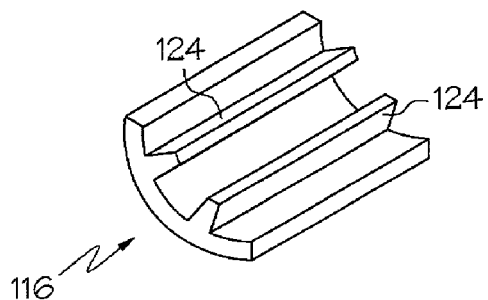
FIG. 20 shows a perspective view of an inflatable member with parts cut-away.

The inflatable member(s) may also constructed from multiple materials of varying rigidity or compliance. These materials may alternate radially around the perimeter of the inflatable member and/or longitudinally along its length. An example of such an inflatable member in a partially expanded state is shown at 116 in FIG. 20. Inflatable member 116 includes a plurality of balloon contacting portions 124. Balloon contacting portions 124 are made of a compliant material, for example nylon, silicon, latex, polyurethane. The remainder of the balloon may be made of non-compliant material, for example, polypropylene, polyimides, polyamides, and polyesters, such as PET and PEN (poly(ethylene napthalenedicarboxylate)). Where an inflatable member such as that shown in FIG. 20 is used, the balloon contacting portions need not be separated by constraining members.

In other embodiments of the invention, such as those shown in FIGS. 1-7, a plurality of inflatable members with balloon contacting portions are provided.

Figure 21:
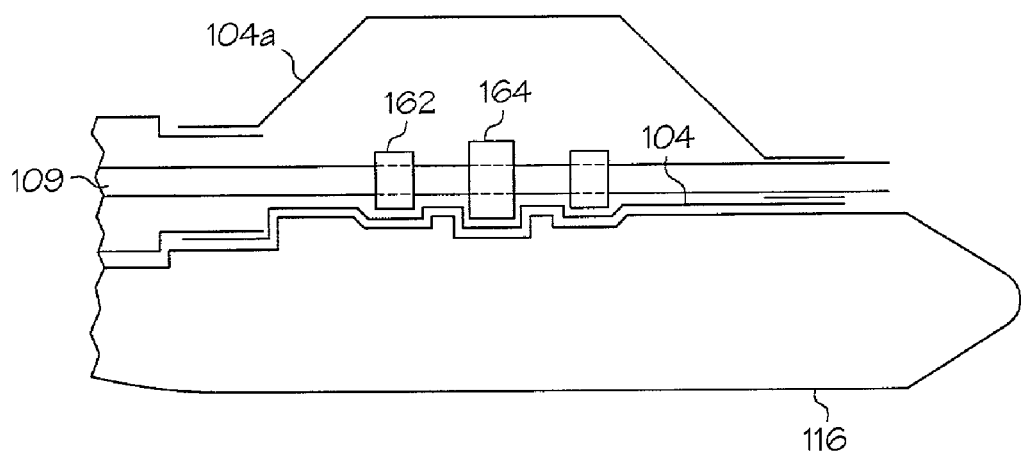
FIG. 21 shows a cross-sectional view of the device of FIG. 14 taken along line 21-21 with parts cut away.

Because the extent to which the inflatable members may be inflated is easily controllable, the inventive devices can be particularly advantageous in configuring balloons where there are structures underlying the balloon such as marker bands, bonds or hubs. As shown in FIG. 21, inflatable member 116 applies a sufficient inward force to deform balloon 104 inward and produce wing 104*a*, and yet conforms to the shape of marker band 162 and hub 164 with minimal likelihood of damage. Also, by varying the extent of inflation of the inflatable members, the inventive devices may be used to configure balloons of different sizes disposed about catheters of varying sizes. To that end, the inventive device may be outfitted with a control system which requires the input of one or more parameters such as the catheter size and/or the location and size of any underlying structure to provide for automatic configuring of balloons.

Figure 22:
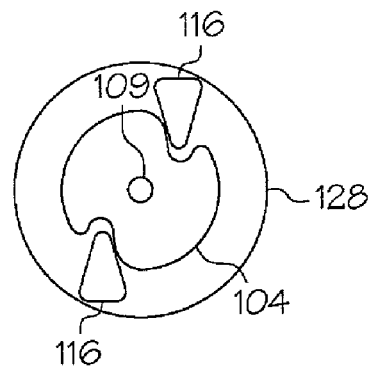
FIG. 22 shows a cross-sectional view of another embodiment of the invention.
Figure 23:
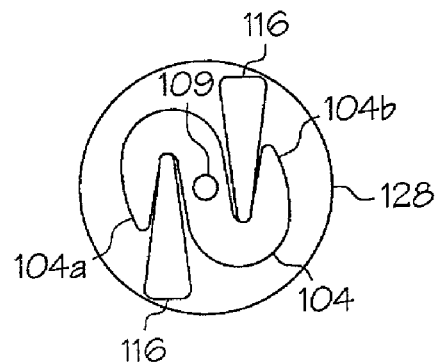
FIG. 23 shows a cross-sectional view of the embodiment of FIG. 22 upon further inflation of the inflatable members.

In the above embodiments, balloon contacting portions 124 apply substantially radially inward forces to medical balloon 104. It is also within the scope of the invention for the balloon contacting portions to apply a force having substantial radial and circumferential components. This may also be achieved, as shown in FIG. 22, by offsetting inflatable members 116 relative to the center of balloon 104. Inflatable members 116, as shown in FIG. 22, are partially inflated and apply a force having both radial and circumferential components to balloon 104. Inflatable members 116 are shown more fully inflated in FIG. 23.

The invention is also directed to any of the inventive devices disclosed herein in combination with a balloon catheter. Desirably, the balloon catheter is disposed in the channel of the inventive devices.

The invention is further directed to inventive methods of configuring a medical balloon. In accordance with one embodiment of the inventive methods, as shown in FIG. 12, medical balloon 104 may be disposed between one or more inflatable members 116, each of which has a balloon contacting portion 124. Any of the inflatable members disclosed herein or any other suitable inflatable members may be used.

As shown in FIG. 12, medical balloon 104 is at least partially inflated by supplying an inflation fluid thereto. An apparatus having a desired number of inflatable members is provided. The number of inflatable members will determine how many pleats are formed in the balloon. Inflatable members 116 are then inflated by delivering an inflation fluid such as a gas or a liquid to the inflatable members so that balloon contacting portions 124 deform portions of medical balloon 104 inward, as shown in FIG. 13. The inflatable members may be inflated simultaneously, sequentially or in any other suitable order. For example, going in a clockwise or counter-clockwise direction about the balloon, inflatable members may be inflated in sequence. Another inflation sequence involves inflating every second inflatable member simultaneously or in sequence and then inflating the remaining inflatable members simultaneously or in sequence.

Optionally, inflatable members 116 may be supplied with a heated inflation fluid to soften the inflatable members 116 so that they are better able to conform to any underlying structure and to, optionally, heat set the wings that are formed. Further, the heated fluid allows softening of medical balloon 104 to facilitate reconfiguration of the balloon.

Next, medical balloon 104 is at least partially deflated by withdrawing at least some of the inflation fluid from the balloon. Desirably, all of the inflation fluid is withdrawn from the balloon and inwardly deformed portions 156 of medical balloon 104 form a plurality of balloon folds. Where the inflatable members are longer than the body portion of the balloon, the folds will desirably extend to the cone sections of the balloon. Finally, inflatable members 116 are removed from about medical balloon 104. This may be accomplished by pulling balloon 104 through opening 148 in optional end cap 132 of optional end support 131.

Typically, as shown in FIG. 8, each of the inflatable members 116 has an inflation lumen 119 with an inflation port 117 which opens into the inflatable member at a first end of the inflatable member and the balloon has an inflation lumen 121 with an inflation port 123 which opens into balloon 104 at an end of the balloon opposite the first end of the inflatable member. Desirably, in accordance with the inventive methods, the inward force is applied progressively along the length of the medical balloon from one end of the balloon to the other end of the balloon. In accordance with the invention, the inflation ports of the inflatable members and the inflation ports of the balloon may be positioned in other locations relative to one another to allow for inflation to occur in other ways as well. For example, where the inflation ports are in the center of the balloon and in the center of the inflatable members, the inward force would be applied progressively outward in both directions from the center of the balloon.

Ideally, the balloon will be completetly evacuated of fluid by means of the external pressure applied by the inflatable members exceeding that of the internal pressure supplied to the balloon. Once the balloon has been evacuated, a moderate vacuum may be drawn prior to the release of pressure from the inflatable members to preserve the shape of the newly configured balloon.

Figure 10:
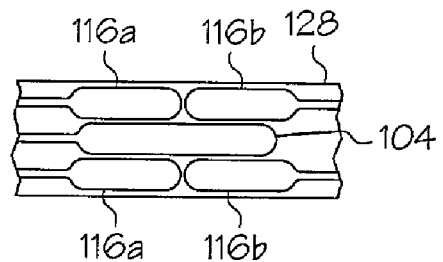
FIG. 10 shows an inventive device including inflatable members disposed end to end along the balloon.

In accordance with the inventive methods, the inflatable members may be inflated simultaneously or in any other predetermined sequence. For example, where the plurality of inflatable members includes a first inflatable member located at a first end of the balloon, a second inflatable member located at the middle of the balloon and a third inflatable member located at a third end of the balloon, as shown in FIG. 10, the second inflatable member(s) may be inflated prior to the first and third inflatable members. Where the inflation port of the balloon is located in the middle of the balloon, the first and third inflatable members may be inflated prior to the second inflatable member(s) to allow some of the inflation fluid to be gradually expelled from the balloon. In another embodiment, the first inflatable member is inflated prior to the second inflatable member which is inflated prior to the third inflatable member. This latter sequence, when practiced on a balloon such as that shown in FIG. 8 with an inflation port at an end, allows for the inflation fluid in the balloon to gradually be expelled from the balloon during the configuring process.

The invention is also directed to a method of configuring at least a portion of a medical balloon comprising the steps of providing a catheter comprising a medical balloon, at least partially inflating the medical balloon, applying a plurality of discrete axially spaced inward forces to the medical balloon and deflating the medical balloon. Suitably, the plurality of discrete forces are applied by a plurality of inflatable members axially spaced along the balloon. The plurality of discrete forces may be applied simultaneously with one another or in a predetermined sequence. Desirably, the plurality of inward forces are applied by inflatable members which have been inflated as discussed above. In some embodiments, the inward forces may be applied by any other member having a balloon contacting surface. Examples of members which may be used include dies including bars and wires.

Typically, the balloon folds formed in accordance with the inventive methods will extend over the entire length of the balloon in an axial direction. The invention also contemplates methods which result in balloon folds which extend over less than the entire balloon and which extend in non-axial directions. As an example of the latter, the balloon folds may be limited to the body portion of the balloon. As another example, where a device such as that shown generally at 100 in FIG. 11a is used, the balloon may be configured with spiral folds.

The invention is also directed to a medical balloon comprising a pleat, at least a portion of which extends in a direction which is non-parallel to the longitudinal axis of the balloon. Typically, the pleat has a first end and a second end, the first end circumferentially and longitudinally displaced from the second end of the pleat. In one embodiment, the pleat spirals at least partially about a longitudinal axis of the balloon. An example of such a balloon having a plurality of spiral pleats 104a and 104b is shown at 104 in FIG. 11b. The balloon may optionally comprise a plurality of pleats each of which has a first end and a second end which is circumferentially and longitudinally displaced from the first end.

Figure 24:
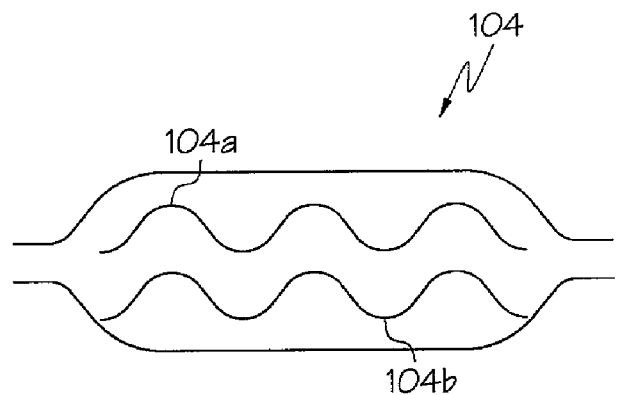
FIG. 24 shows a side elevational view of an inventive medical balloon.

Another example of such a balloon is shown at 104 in FIG. 24. Balloon 104 has a plurality of pleats including pleats 104a and 104b which are wavy. The inventive balloons may have only a single wavy pleat or two, three, four, five, six or more wavy pleats.

The balloon of FIG. 24 may be made using the inventive methods disclosed above where each of the inflatable members have a curved shape which corresponds to the shape of the pleats shown in FIG. 24. The inventive balloons may also be made by utilizing a plurality of individual inflatable members which are substantially linear in shape and which are arranged end-to-end to form pleats such as those shown in FIG. 24.

The invention is also directed to a medical balloon having a body portion with a first region with pleating and a second region with pleating where the second region is axially displaced from the first region and the pleating in the second region differs in appearance from the pleating in the first region. An example of such a balloon is shown in FIG. 24. The pleating in the second region may also differ in appearance from that of the first region as a result of discontinuities between the pleating in the first and second regions. The appearance of the pleating in the first and second regions may also differ in that the number of pleats in the first region differs from the number of pleats in the second region. It is also within the scope of the invention for the shape of the pleating in the different regions to differ. The medical balloon may optionally comprise additional pleated regions where the appearance of the pleating differs from the appearance of the pleating in other regions.

The invention is also directed to a device for configuring a medical balloon which is capable of applying a plurality of discrete, axially spaced inward forces to a medical balloon. The device comprises two or more axially spaced dies. The device may comprise a single line of dies disposed parallel to the longitudinal axis of the device which impart a single fold in a balloon or may comprise a plurality of lines of dies disposed parallel to the longitudinal axis of the device which are capable of providing a plurality of folds in a balloon. Optionally, the dies may be both axially and circumferentially spaced from one another about the longitudinal axis of the device. In one embodiment of the invention, the dies are provided in one or more helical arrangements about the longitudinal axis of the device so as to be capable of imparting helical folds in a balloon.

Any of the inflatable members described herein may be used. Where inflatable members are used for dies, each of the inflatable members will include an inflation lumen which may be supplied with an inflation fluid from a source of inflation fluid. One or more controllers may also be supplied to control the flow of inflation fluid to the inflatable members.

Figure 25:
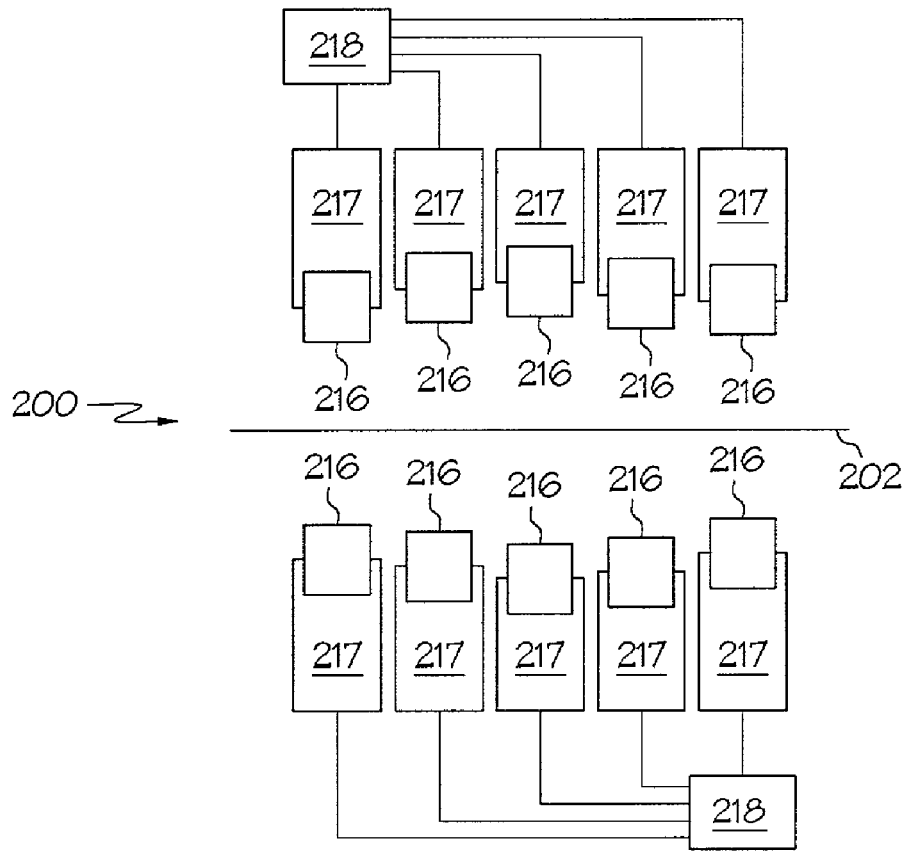
FIG. 25 shows a cross-sectional view of an inventive device for configuring medical balloons.
Figure 26:
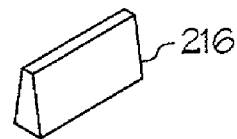
FIG. 26 shows a perspective view of a die.

In one embodiment of the invention, as shown in cross-sectional view in FIG. 25, device 200 includes non-inflatable dies 216 which are used to configure a medical balloon. The longitudinal axis of the device, along which a medical balloon may be disposed, is shown at 202. Desirably, the dies terminate in edges which are sufficiently smooth to avoid damaging the balloon. The non-inflatable dies may be made of metal, polymeric material or any other suitable material. A perspective view of a suitable die is shown at 216 in FIG. 26.

As shown in FIG. 25, each die 216 extends from a piston 217. Each piston is, in turn, controlled by controller 218. The pistons may be individually controlled or may be controlled in unison.

In other embodiments of the invention, the dies are moved using other devices. For example, the dies may be connected to one or more cam mechanisms such as the cam mechanisms disclosed in WO 0121103.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2 or claim 1, claim 5 may be taken as alternatively dependent from claim 2 or claim 1; etc.).

The invention claimed is:

1. A device for configuring an inflatable balloon of a balloon catheter assembly, the device comprising:
a body comprising a plurality of inflatable members defining a channel therebetween, the plurality of inflatable members disposed about the channel and configured to contain at least a portion of an inflatable balloon of a balloon catheter within the channel, each inflatable member having a balloon contacting portion,
wherein each inflatable member extends part of the way about the channel but does not encircle the channel; and
a housing configured to constrain the plurality of inflatable members as the plurality of inflatable members inflate inwardly into the channel.

2. The device of claim 1 wherein the inflatable members are disposed about the circumference of a circle.

3. The device of claim 1 comprising at least three inflatable members.

4. The device of claim 3 wherein the inflatable members are generally tubular and have a circular cross-section.

5. The device of claim 3 wherein the body further comprises a rigid tube in which the plurality of inflatable members are constrained, the tube having a first end with a first opening and a second end with a second opening and a passage therethrough.

6. The device of claim 5 further comprising first and second end caps, the first end cap disposed at the first end of the tube across the first opening and the second end cap disposed at the second end of the tube across the second opening.

7. The device of claim 6 wherein the inflatable members extend from the first and second end caps, the inflatable members in relative alignment with one another, the first and second end caps supporting the inflatable members.

8. The device of claim 7 wherein the first end cap has an opening therethrough sized to receive at least a portion of a balloon catheter therethrough.

9. A method of configuring at least a portion of a medical balloon comprising the steps of:
providing a device as in claim 7;
disposing a medical balloon between the inflatable members;
at least partially inflating the medical balloon;
inflating the inflatable members so that the balloon contacting portions deform portions of the medical balloon inward;
at least partially deflating the medical balloon, the inwardly deformed portions of the medical balloon forming a plurality of balloon folds.

10. The method of claim 9 wherein each of the balloon folds extends along the entire length of the balloon.

11. The method of claim 10 wherein each of the balloon folds extends spirally about the balloon.

12. The device of claim 1 wherein the plurality of inflatable members includes at least two inflatable members disposed end-to-end along the length of the channel.

13. The device of claim 1 wherein the plurality of inflatable members are disposed in one or more spirals about the channel.

14. The device of claim 1 wherein the plurality of inflatable members includes at least two inflatable members which are circumferentially and axially displaced from one another.

15. The device of claim 14 wherein the inflatable members which are circumferentially and axially displaced from one another are shorter in length than the balloon.

16. The device of claim 1 wherein each of the inflatable members has an inflation lumen which opens into the inflatable member at a first end of the device and the balloon has an inflation lumen which opens into the balloon at a second end of the device opposite the first end of the device.

17. A method of configuring at least a portion of a medical balloon comprising the steps of:
providing a device as in claim 16;
disposing a medical balloon between the inflatable members;
at least partially inflating the medical balloon;
inflating the inflatable members so that the balloon contacting portions progressively deform portions of the medical balloon inward starting from the first end of the device;
at least partially deflating the medical balloon, the inwardly deformed portions of the medical balloon forming a plurality of balloon folds; and
removing the inflatable members from about the medical balloon.

18. The method of claim 17 wherein each of the balloon folds extends along the entire length of the balloon.

19. The method of claim 17 wherein each of the balloon folds extends spirally about the balloon.

20. The device of claim 1 further comprising at least one constraining member disposed between adjacent balloon contacting portions.

21. The device of claim 20 wherein the constraining member is in the form of a slat.

22. The device of claim 1 wherein the balloon contacting portion is made of a compliant material and the remainder of the inflatable member is made of a non-compliant material.

23. The device of claim 1 wherein the inflatable member has an inflation lumen which opens into the inflatable member at a first end of the device and the balloon has an inflation lumen which opens into the balloon at a second end of the device opposite the first end of the device.

24. A device for configuring an inflatable balloon of a balloon catheter assembly, the device comprising:
a body comprising a plurality of independently inflatable members defining a channel therebetween, the inflatable members arranged side-by-side about the channel, each of the inflatable members extending only part of the way about the channel, the plurality of independently inflatable members disposed about the channel and configured to contain at least a portion of an inflatable balloon of a balloon catheter within the channel, the independently inflatable members inflatable inward to reduce the size of the channel, and
a housing configured to constrain the plurality of inflatable members as the plurality of inflatable members inflate inwardly into the channel.

25. In combination, a device for configuring an inflatable balloon of a balloon catheter assembly and a balloon portion of a balloon catheter assembly, the device comprising:
a body comprising a plurality of inflatable members defining a channel therebetween, the plurality of inflatable members disposed about the channel and configured to contain at least a portion of an inflatable balloon of a balloon catheter within the channel, the inflatable members inflatable from a first size to a second size in which the inflatable members apply an inward force to a balloon of a balloon catheter assembly disposed in the channel, the inflatable members arranged side-by-side about the channel, each of the inflatable members extending only part of the way about the channel, wherein
the balloon portion of a balloon catheter assembly is removably disposed in the channel.

26. A device for configuring an expandable member for use in a bodily vessel comprising:
a body comprising a plurality of inflatable members defining a channel therebetween, the plurality of inflatable members disposed about the channel and configured to contain at least a portion of the expandable member within the channel, the inflatable members inflatable inward so as to reduce in area a cross-section of the channel, the cross-section extending perpendicular to a longitudinal axis of the channel, and the inflatable members arranged side-by-side about the channel, each of the inflatable members extending only part of the way about the channel.

27. The device of claim 26 wherein the body further comprises a rigid tube in which the plurality of inflatable members are constrained, the tube having a first end with a first opening and a second end with a second opening and a passage therethrough.

28. The device of claim 27 wherein the rigid tube is disposed between first and second end supports, at least one of the first and second end supports having an opening therethrough to provide access to the channel.

29. The device of claim 27 wherein the rigid tube is disposed between first and second end supports, at least one of the first and second end supports having an opening therethrough to provide access to the channel.

* * * * *